(12) United States Patent
Soane et al.

(10) Patent No.: US 6,176,962 B1
(45) Date of Patent: Jan. 23, 2001

(54) METHODS FOR FABRICATING ENCLOSED MICROCHANNEL STRUCTURES

(75) Inventors: David S. Soane; Zoya M. Soane, both of Piedmont; Herbert H. Hooper, Belmont; M. Goretty Alonso Amigo, Santa Clara, all of CA (US)

(73) Assignee: Aclara Biosciences, Inc., Mountain View, CA (US)

( * ) Notice: Under 35 U.S.C. 154(b), the term of this patent shall be extended for 0 days.

(21) Appl. No.: 08/878,437

(22) Filed: Jun. 18, 1997

Related U.S. Application Data (63) Continuation-in-part of application No. 08/853,661, filed on May 9, 1997, which is a continuation-in-part of application No. 08/832,790, filed on Apr. 4, 1997, which is a continuation-in-part of application No. 08/627,484, filed on Apr. 4, 1996, now Pat. No. 5,858,188, which is a continuation-in-part of application No. 08/430,134, filed on Feb. 26, 1995, now abandoned, which is a continuation of application No. 08/196,763, filed on Feb. 14, 1994, now abandoned, which is a continuation of application No. 07/880,187, filed on May 7, 1992, now abandoned, which is a continuation of application No. 07/487,021, filed on Feb. 28, 1990, now Pat. No. 5,126,022, and a continuation-in-part of application No. 08/615,642, filed on Mar. 13, 1996, now Pat. No. 5,750,015, which is a continuation-in-part of application No. 08/430,134, filed on Apr. 26, 1995, now abandoned, and a continuation-in-part of application No. 08/715,338, filed on Sep. 18, 1996, now Pat. No. 5,935,401, and a continuation-in-part of application No. 08/690,307, filed on Jul. 30, 1996, now Pat. No. 5,770,029.

(51) Int. Cl.$^7$ ........................................................ B32B 31/00
(52) U.S. Cl. ........................................ 156/292; 156/273.5
(58) Field of Search ................................. 156/292, 273.5

(56) References Cited

U.S. PATENT DOCUMENTS

| | | | |
|---|---|---|---|
| 4,680,201 | 7/1987 | Hjerten | 427/230 |
| 4,756,884 | 7/1988 | Hillman et al. | 422/73 |
| 4,875,956 | 10/1989 | Brackett | 156/84 |
| 4,891,120 | 1/1990 | Sethi et al. | 204/299 R |
| 4,908,112 | 3/1990 | Pace | 204/299 |
| 4,999,069 | 3/1991 | Brackett et al. | 156/84 |
| 5,061,381 | 10/1991 | Burd | 210/789 |
| 5,250,263 | 10/1993 | Manz | 422/81 |
| 5,376,252 | 12/1994 | Ekstrom et al. | 204/299 |
| 5,433,898 | 7/1995 | Thakrar et al. | 264/1.7 |
| 5,571,410 | 11/1996 | Swedberg et al. | 210/198.2 |

FOREIGN PATENT DOCUMENTS

| | | |
|---|---|---|
| 0 452 055 B1 | 4/1991 | (EP) . |
| 0 620 432 A1 | 10/1994 | (EP) . |
| 0 665 430 A1 | 8/1995 | (EP) . |
| WO 94/29400 | 12/1994 | (WO) . |
| WO 96/04547 | 2/1996 | (WO) . |
| WO 96/29629 | 9/1996 | (WO) . |
| WO 97/06012 | 2/1997 | (WO) . |
| WO 97/06013 | 2/1997 | (WO) . |

OTHER PUBLICATIONS

Nielen, "Capillary Zone Electrophoresis Using a Hollow Polypropylene Fiber," *J. High Res. Chrom.*, (1993), vol. 16, pp. 62–64.

(List continued on next page.)

*Primary Examiner*—Francis J. Lorin
(74) *Attorney, Agent, or Firm*—Bertram Rowland; Rae-Venter Law Group, P.C.

(57) ABSTRACT

Methods are provided for the fabrication of polymeric microchannel structures having enclosed microchannels of capillary dimension. The microchannel structures are constructed of a base plate and a cover, sealed together. Microchannel structures having walls of a plastic material are formed in a generally planar surface of at least the base plate. The cover has at least one generally planar surface, and the microchannel structures are enclosed by bonding the planar surfaces of the cover and the base plate together. In some embodiments the surfaces of the cover and base plate are both of plastic material, and are directly thermally bonded. In some embodiments a bonding material is applied to one of the surface prior to bringing the surfaces together. Suitable bonding materials are disclosed.

17 Claims, 5 Drawing Sheets

OTHER PUBLICATIONS

Liu et al., "Polymeric Hollow Fibers for Capillary Electrophoresis," *J. Microcol.*, (1993), vol. 5, No. 3, pp. 243–253.

Hjerten, "High–Performance Electrophoresis Elimination of Electroendosmosis and Solute Adsorption," *J. Chrom.*, (1995), 347, pp. 191–198.

"Adhesion and Bonding" In: *Enclycopedia of Polymer Science and Engineering, Wiley Interscience*, (1995) vol. 1, vol. 1, pp. 476–517.

Gilges et al., "Capillary Zone Electrophoresis Separations of Basic and Acidic Proteins Using Poly(vinyl alcohol) Coatings in Fused Silica Capillaries," *Anal. Chem.*, (1994), vol. 66, No. 13, pp. 2038–2046.

Ratner, "Surface modification of polymers: chemical, biological and surface analytical challenges," *Biosensors & Bioelectronis*, (1995) 10, pp. 797–804.

VerLee et al., "Fluid Circuit Technology: Integrated Interconnect Technology for Miniature Fluidic Devices," *Solid–State Sensor and Actuator Workshop—Hilton Head, S.C.*, (Jun. 2–6, 1996), pp. 9–14.

Schutzner et al., "Electrophoresis in Synthetic Organic Polymer Capillaries: Variation of Electroosmotic Velocity and Potential with pH and Solvent Composition," *Anal. Chem*, (1992), vol. 64, No. 17.

Tomlinson et al., "Improved On–Line Membrane Preconcentration–Capillary Electrophoresis (mPC–CE), " *J. High Res. Chrom.* (1995) 18:381–3.

Barron & Blanch, "DNA Separations by Slab Gel and Capillary Electrophoresis: Theory and Practice," *Separation and Purification Methods* (1995) 24:1–118.

K. Hofmann et al., "Avidin Binding of Carboxyl–Substituted Biotin and Analogues," (1982), Biochemisty vol. 21, pp. 978–984.

Simpson et al., "Microfabricated Capillary Array Electrophoresis Device and Method," 1997.

Wooley et al., "Ultra–high–speed DNA fragment separations using Microfabricated capillary array electrophoresis chips," *PNAS USA*, (1994), vol. 91, pp. 11348–11352.

Guzman, "Biomedical applications of on–line preconcentration–capillary electrophoresis using an analyte concentrator:; investigation of design options," *J. Liquid Chro.* (1995), pp. 3751–3768.

Cole et al., "Selective preconcentration for capillary zone electrophoresis using protein G immunoaffinity capillary chromatography," *Electophoresis* (1995), pp. 549–556.

Cai et al., "Selective On–Line Preconcentration of Proteins by Tandem Metal Chelate Capillaries–Capillary Zone Electrophoresis," *J. Liquid Chro.* (1993), pp. 2007–2004.

Cai et al., "On–Line Preconcentration of Triazine Herbicides with Tandem Octadecyl Capillaries–Capillary Zone Electrophoresis," *J. Liquid Chrom.* pp. 1179–1192.

Kasicka et al., "Isotachophoretic Electrodesorption of Proteins From an Affinity Adsorbent on a Microscale," *J. Chrom.* (1983), pp. 117–128.

Stegehuis et al., "Isotachophoresis as an on–line concentration pretreatment technique in capillary electrophoresis," *J. Chrom.* (1991), pp. 393–402.

Chien et al., "Field amplified sample injection in high–performance capillary electrophoresis," *J. Chrom.* (1991), pp. 141–152.

Beckers et al., "Effect of sample stacking on resolution, calibration graphs and pH in capillary zone electrophoresis," *J. Chrom.* (1993), pp. 371–378.

Effenhauser et al., "High–Speed Separation of Antisense Oligonucleotides on a Micromachined Capillary Electrophoresis Device," *Anal. Chem.* (1994), pp. 2949–2953.

Jacobson et al., "Precolumn Reactions with Electophretic Analysis Integrated on a Microchip," *Anal. Chem.* (1994), pp. 4127–4132.

Harrison et al., "Micromachining a Miniaturized Capillary Electrophoresis–Based Chemical Analysis System on a Chip," *Science* (1993), vol. 261, pp. 895–897.

Tomlinson et al., "Enchancement of concentration limits of detection in CE and CE–MS: A review of on–line sample extraction, clean–up, analyte preconcentration, and microreactor technology," *J. Cap. Elc.* (1995) pp. 247–266.

METHODS FOR FABRICATING ENCLOSED MICROCHANNEL STRUCTURES

This application is a Continuation-in-part of Ser. No. 08/853,661 filed May 9, 1997, which is a Continuation-in-part of Ser. No. 08/832,790, filed Apr. 4, 1997, which is a Continuation-in-part of Ser. No. 08/627,484, filed Apr. 4, 1996, now U.S. Pat. No. 5,858,188,which is a Continuation-in-part of Ser. No. 08/430,134, filed Feb. 26, 1995, abandoned, which was a Continuation of Ser. No. 08/196, 763, filed Feb. 14, 1994, abandoned, which was a Continuation of Ser. No. 07/880,187, filed may 7, 1992, abandoned, which was a Continuation of Ser. No. 07/487,021, filed Feb. 28, 1990, now U.S. Pat. No. 5,126,022; and this application is also a Continuation-in-part of Ser. No. 08/615,642, filed Mar. 13, 1996 now U.S. Pat. No. 5,750,015, which is a Continuation-in-part of Ser. No. 08/430,134, supra; and this application is further a Continuation-in-part of Ser. No. 08/715,338, filed Sep. 18, 1996 now U.S. Pat. No. 5,935, 401; and this application is a Continuation-in-part of Ser. No. 08/690,307, filed Jul. 30, 1996, now U.S. Pat. No. 5,770,029. The foregoing U.S. patent applications are hereby incorporated herein by reference in their entirety.

BACKGROUND

This invention relates to construction of microchannel structures for use in microfluidic manipulations.

Microchannel structures are of great interest for applications involving the manipulation of small fluid volumes, such as chemical and biochemical analysis. Various microchannel structures having channel dimensions on the order of one or a few millimeters have been used for chemical and biochemical assays.

These structures are typically produced by injection molding using various thermoplastic polymers. Injection molding is an economical process, and a variety of thermoplastics having good optical and mechanical properties can be processed by injection molding to form the desired structures. The injection molding process involves introducing a molten thermoplastic material into a mold cavity, and then cooling the cavity to solidify the resin. In the case of forming microchannel structures, a mold having the negative pattern of the desired channel structures must be created. Conventional tooling methods can be used to create molds for channels having dimensions as small as about 1 mm. Typically, enclosed microchannels are desired for the final structure. A common method for enclosing microchannel structures formed in plastics is to join a base and cover substrate using sonic welding. In addition, certain adhesives can also be used to join the base and cover substrates.

It has become desirable to create microchannel structures having capillary dimensions, i.e., having dimensions ranging from less than 1 micron to upwards of 1 mm. These structures are of interest for manipulating very small fluid volumes through the application of electric fields to perform electrofluidics, i.e., the movement of fluids in microchannels utilizing electrokinetic flow, that is, electrophoresis and/or electroosmotic flow (EOF). Electrophoresis is the movement of individual charged particles or molecules in response to the application of an electric field to an ionic solution. Electroosmotic flow is a bulk fluid flow (individual ions plus solvent molecules) that also results from the application of an electric field to an ionic solution. The extent of the bulk fluid flow is a function of the charge on the wall of the channel, as well as the viscosity of the solution. Both EOF and electrophoresis can be used to transport substances from one point to another within the microchannel device.

To create microchannels having capillary dimensions, photolithography in silicon or glass substrates has been employed. See, e.g., U.S. Pat. No. 4,908,112, U.S. Pat. No. 5,250,263. In the case of fused silica, these structures can be enclosed by anodic bonding of a base and cover substrate.

Although microchannel structures of such materials have been produced, it would be much more economical, and therefore desirable, to produce structures of capillary dimensions in polymeric materials or plastics. However, the conventional methods for forming and enclosing channels in plastic do not provide the accuracy and precision required for structures of capillary dimensions. For example, when using sonic welding, heating and deformation may occur in the channel regions. When the edges of a sonic weld are uneven, poor electrofluidic performance may result. Furthermore, sonic welding of highly defined intersections of capillary dimensions is not easily accomplished with adequate fidelity. Similarly, with conventional adhesive methods, the adhesive material may flow into and plug the channels.

Thus, there is interest in the development of new methods of fabricating polymeric microstructures, specifically in new methods of sealing the cover and base plates together, where such new methods do not result in deformation or filling in of the microchannels enclosed in the structure. Ideally, such methods should be simple and readily reproducible so as to be suitable for large scale manufacturing.

U.S. Pat. No. 5,376,252 to Eckstrom et al. describes a process for creating capillary size channels in plastic using elastomeric spacing layers. Öhman International Patent Publication WO 94/29400 describes a method for producing microchannel structures involving the application of a thin layer of a thermoplastic material to one or both of the surfaces to be joined, then joining the surfaces and heating the joined parts to melt the thermoplastic bonding layer.

SUMMARY OF THE INVENTION

Methods are provided for the fabrication of polymeric microchannel structures having enclosed microchannels of capillary dimension. The microchannel structures are constructed of a base plate and a cover, sealed together. Microchannel structures having walls of a plastic material are formed in a generally planar surface of at least the base plate. The cover has at least one generally planar surface, and the microchannel structures are enclosed by bonding the planar surfaces of the cover and the base plate together. The microchannel structures according to the invention find use in a variety of applications, particularly in electrofluidic applications.

Approaches to sealing the cover and base plate according to the invention include thermal bonding of the base plate and cover surfaces, and use of a bonding material between the base plate and cover surfaces. Suitable bonding materials include elastomeric adhesive materials, and activatable bonding materials, including liquid curable adhesive materials and thermo-melting adhesive materials.

The thermal bonding approach can be employed where the apposing planar surfaces of the base plate and the cover are made of similar polymeric materials. Generally, in this approach, the planar surfaces of the base plate and the cover are aligned and confined to a mechanical fixture, in which they are progressively heated under pressure to a temperature 2–5° C. above the glass transition temperature of the polymer. In this first step, small irregularities in the surfaces accommodate to each other, while maintaining the physical integrity of the channels. Then, the temperature is maintained above the glass transition temperature of the polymer for a time sufficient to allow the polymer molecules to interpenetrate the two surfaces and create a morphological bonding. Above the glass transition temperature the molecules have sufficient entropy to entangle and orient in the surfaces of the two plates. In a final step of the bonding process the temperature is slowly reduced in order to maintain a stress free interface that provides a stable assembled microchannel structure.

Bonding materials can be employed where the apposing planar surfaces of the base plate and the cover are made either of similar or of different materials.

In approaches employing thermo-melting adhesives, the adhesive formulation includes medium molecular weight components that upon heating melt and diffuse into the two apposed surfaces, interpenetrating the two surfaces and creating a stable interface for the assembled microchannel structure. Suitable thermo-melting adhesives are usually formulated with chemistries that provide secondary bond interactions (e.g., hydrogen bonding, Van der Waals forces, and hydrophobic forces) between the surfaces being bonded and the adhesive.

In approaches using liquid curable materials, one of the planar surfaces (usually of the cover), is coated with a layer or film of a liquid, curable adhesive material. The fluid layer is then rendered non-flowable, after which the coated surface is contacted with the apposing planar surface (usually of the base plate in which the microchannels have been formed). Then the curable adhesive material is cured to seal the surfaces together, forming the enclosed microchannel structure.

In approaches employing elastomeric bonding materials, the adhesive layer or film is a rubber or elastomer material (e.g., natural and synthetic rubbers, polyurethane, polysulfides and silicones). The elastomeric bonding material can be applied in solution, as an emulsion, or in formulations of two reactive components. Elastomeric bonding materials can be used in contact adhesive formulations, in which one or more small molecule components are admixed to provide tack; the do not require application of pressure to establish bonding. Or, elastomeric bonding materials can be used as pure elastomers to provide closure of the microchannel structures and to seal small irregularities in the generally planar apposed surfaces by application of pressure to exploit the compressibility of the elastomeric materials.

In some preferred methods according to the invention, the bonding process results in interpenetration into the two apposed planar surfaces, providing a stable sealed interface between the base plate and cover. Where a bonding material is used, a thin film or layer of the bonding material at the interface results.

DETAILED DESCRIPTION

The invention is now described in further detail, beginning with a description of the microchannel structures that are constructed according to the methods of the invention, followed by a discussion of the methods themselves.

The microchannel structures produced by the subject methods include at least one enclosed polymeric microchannel of capillary dimension. Thus, the structure may comprise a single enclosed microchannel or a network of interconnecting or separate microchannels having a variety of different configurations. Although the subject microchannels are enclosed, the enclosed channels will comprise at least one means of introducing liquid into the internal volume of the channel.

A microchannel of "capillary dimension", as that term is used herein, has cross-sectional dimensions that provide for capillary flow along the channel; usually a wider cross-sectional dimension of the channel is in the range about 50 $\mu$m to 750 $\mu$m, usually from about 100 $\mu$m to 500 $\mu$m and more usually from about 100 $\mu$m to 250 $\mu$m; a narrower cross-sectional dimension (usually the depth of the channel) can be somewhat smaller.

A "polymeric microchannel", as that term is used herein is a microchannel in which at least the inner surfaces of the microchannel walls, i.e., that surface that contacts the liquid that is transported in the channel when in use, is of a polymeric material, where the thickness of the polymeric material will be at least about 1 $\mu$m, usually at least about 5 $\mu$m, and more usually at least about 50 $\mu$m, where the thickness may be as great as 5 mm or greater.

The structures may take a variety of different shapes; they may, for example, be including disc-like or card-like, and they may be layered or laminated "sandwich" structures. Representative shapes for such structures are further described in, for example, U.S. patent applications Ser. Nos. 08/853,661 and 08/715,338 and U.S. Pat. Nos. 5,750,015 and 5,770,029.

In general, the microchannel structures according to the invention are constructed of two parts, each having at least one generally planar surface, sealed together so that the generally planar surfaces are apposed. One part is referred to as a base plate, and the other is referred to as a cover. The planar surface of the base plate includes one or more microchannels, while the planar surface of the cover may or may not include one or more microchannels. The cover may be a more or less rigid plate, or it may be a film, and the thickness of the cover may be different for materials having different mechanical properties. Usually the cover ranges in thickness from at least about 200 μm, more usually at least about 500 μm, to as thick as usually about 5 mm or thicker, more usually about 2 mm. The cover substrate may be fabricated from a single material or be fabricated as a composite material. In some embodiments the cover is of a plastic material, and it may be rigid or elastomeric.

Both the base and cover substrates can be fabricated using any convenient methodology, such as molding, casting, extrusion sheet forming, calendaring, thermoforming, and the like. Suitable base and cover substrates for use in the subject invention are further described in U.S. patent applications Ser. Nos. 08/853,661 and 08/715,338 and U.S. Pat. Nos. 5,750,015 and 5,770,029.

Any of a variety of microchannel patterns, device shapes, and substrate materials can be used to construct and assemble the components of the microfluidic systems according to the invention, so long the device includes at least a generally planar base plate containing microchannels constructed of a plastic material. For example, a base plate and cover plate constructed of a plastic material can be bonded together directly (for example by thermal bonding), or by use of an adhesive layer. Or, a base plate constructed of a plastic material, in which the microchannels are formed, can be covered with a glass plate to enclose the channels, and sealed with an elastomeric film of, for example, a silicon or polyurethane elastomer. Glass provides improved dissipation of heat and better optical properties, as compared with plastic. Or, the device can be formed as a laminate (sandwich structure).

Figure 1:
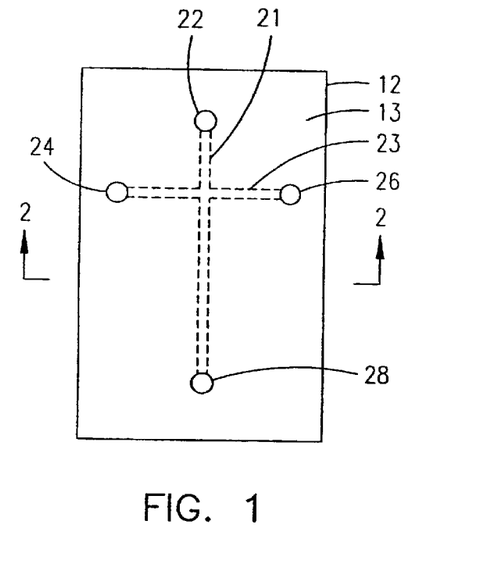
FIG. 1 is a diagrammatic sketch in plan view of a base plate having a microchannel structure on one surface, which may be bonded to a cover according to the invention.
Figure 2:
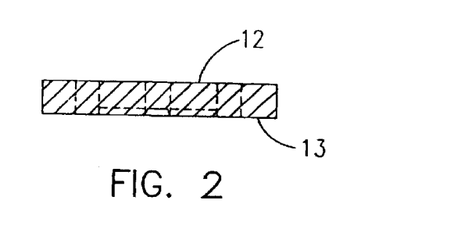
FIG. 2 is a diagrammatic sketch in sectional view thru the base plate of FIG. 1 at 2—2.
Figure 3:
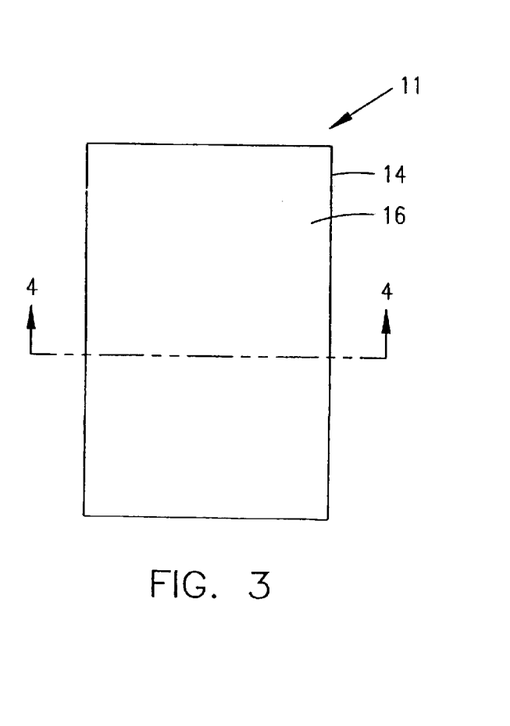
FIG. 3 is a diagrammatic sketch in plan view of a cover having a film of a bonding material on one surface, which may be bonded to a base plate according to the invention.
Figure 4:
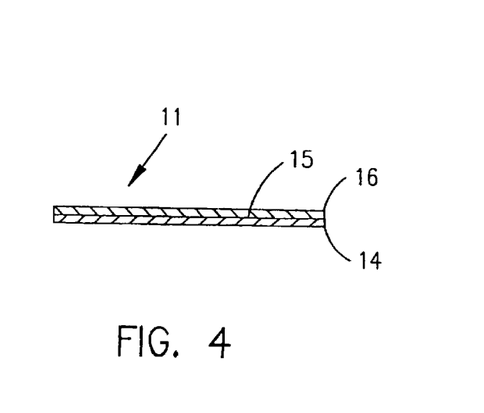
FIG. 4 is a diagrammatic sketch in sectional view thru the cover of FIG. 3 at 4—4.
Figure 5:
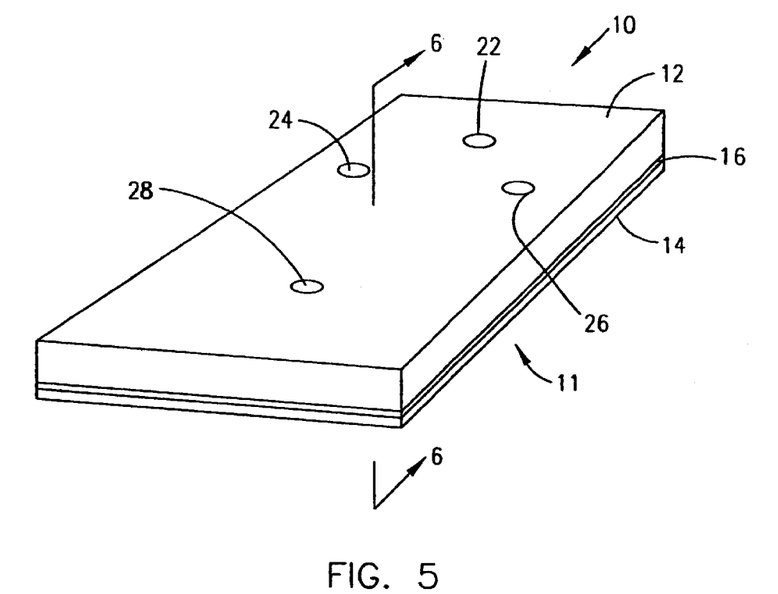
FIG. 5 is a diagrammatic sketch in perspective view of a closed microchannel device fabricated by apposing and bonding the cover of FIGS. 3, 4 onto the base plate of FIGS. 1, 2 according to the invention.
Figure 6:
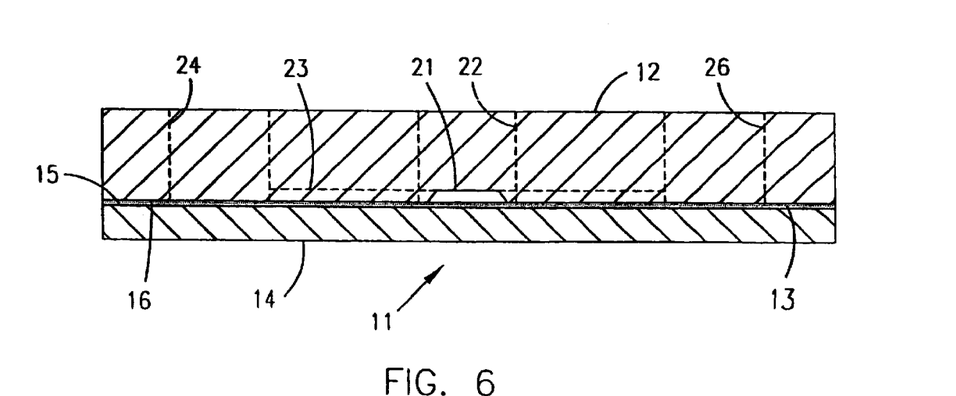
FIG. 6 is a diagrammatic sketch in sectional view thru the microchannel device of FIG. 5 at 6—6.

Construction of microchannel structures by bonding a base plate and a cover according to the invention will now be further described by reference for illustrative purposes to FIGS. 1–6, in which FIGS. 5 and 6 show an assembled microchannel device 10 made by bonding a base plate 12, shown in plan and sectional views in FIGS. 1 and 2 to a cover 14, shown in plan and sectional views in FIGS. 3 and 4, using a bonding material 16. As will be appreciated, the drawings of the exemplary microchannel structures are not to scale and, in particular, certain dimensions (for example the thicknesses of the base plate, the cover, and the bonding material layer; and the sizes of the microchannels and reservoir holes) are shown in extremely exaggerated scale.

Base 12 has a planar surface 13 in which a microchannel structure is formed, including intersecting linear microchannels 21, 23. At the ends of the channels holes 22, 24, 26, 28 are bored through, to provide reservoirs for fluids to be moved within the channels. Techniques for forming the microchannel structure in the base plate are disclosed, for example, in U.S. patent application Ser. No. 08/853,661. The microchannels as formed in the base plate are open, that is, absent a cover apposed to the channel-bearing surface 13 of the base plate, the microchannels are not fully enclosed.

Cover 11 has a generally planar surface 15, apposable onto the channel-bearing surface 13 of base plate 12, onto which a thin film 16 of a bonding material is applied. Microchannel device 10 is formed by apposing the surfaces 13, 15 with the bonding material between them. As a result, the microchannels 21, 23 are closed, having three walls formed in the base plate surface 13, and a fourth wall formed by the cover 11, with the bonding material film 16 constituting the surface of the fourth microchannel wall.

Reservoirs formed as described above are open on a surface of the base plate opposite the surface apposed to the cover. Other constructions may alternatively be employed for providing reservoirs. For example, holes can be bored only partway through the base plate at the ends of the channels, so that the reservoirs are not open on the opposite surface of the base plate; and holes can be bored or cut through the cover, aligned with the reservoirs. Liquids can be added to reservoirs formed in this manner can by filling through the holes in the cover, rather than from the opposite side.

In a method employing a curable bonding material according to the invention, a bonding material is applied onto a planar surface 15 of the cover material 14 to form a layer or film 16. The bonding material may be, for example, a fluid curable adhesive, or a fluid component reactive with the cover material 14 and/or with the base plate material 12, a meltable adhesive film, or a cured elastomeric film that provides physical or chemical characteristics to bind to the base plate in which at least one microchannel is formed.

Some care must be taken to apply the bonding material as a layer or film that is sufficiently thick and uniform to ensure that a continuous strong bond can form between the cover and the base plate at all points adjacent all the microchannels; and not so thick that too much of the bonding material adjacent the microchannels is displaced into the channels, distorting the channel shape or dimensions. An ideal thickness for the bonding material layer or film will accordingly be different for different bonding materials. In practice, generally, the bonding material usually is applied to a thickness at least about 0.5 μm, in some embodiments at least about 1 μm, and in still other embodiments at least about 2 μm.

The bonding material layer or film may be applied to the surface using any convenient means suitable for application of a fluid layer to the surface of substrate. Such means finding use in the subject method therefore include: spin coating, dip coating, knife coating, drawing, rolling, mechanical spraying, atomization, patterned discharge, stamping, silk screening, lamination and the like, with the particular method employed being at least partially dependent on the nature of the substrate, e.g., patterned discharge, stamping and lamination techniques being suited for use with flexible substrate materials.

As mentioned above, in some embodiments the apposed surfaces of the cover and base plate are bonded together according to the invention using a liquid curable adhesive. In these embodiments the adhesive is applied to one surface as a thin film. Accordingly, suitable fluid curable adhesives are flowable, having a viscosity in the range about 50 cp to 15,000 cp, usually about 50 cp to 10,000 cp, and more usually about 100 cp to 5,000 cp, where the viscosity is the viscosity of the material as measured at a temperature between about 15° C. and 50° C.

Any of a variety of bonding materials can be useful in constructing microchannel structures according to the invention. Curable bonding materials can be particularly useful.

Curable bonding materials include materials applicable to all or a part of the substrate surface as a layer, coating, film, etc., which upon application of energy result in formation of a durable stable interface material between the cover and the base materials. The durable stable interface material can be formed by covalent bonding, or interpenetration of the surface materials, or strong physical interaction, or by some combination of these. The energy can be one or a combination of heat, light, or other radiation including infrared or microwave radiation, for example; electron or other particle beam, and the like.

In some embodiments, where the movements of fluids or the progress of reactions within the microchannels are to be detected by means of light transmitted from the sample materials within the microchannel structure out through the cover or through the base plate, certain optical requirements must be met. Preferred modes of light detection may be based for example on UV and visible, luminescence and fluorescence responses of the sample material to incident radiation. For example, any material used in fabricating the cover, the base plate, or the bonding material on an enclosing wall of the microchannel should have good optical transmittance, generally allowing at least about 50%, in some embodiments at least about 20%, and in still other embodiments at least about 10% transmittance. And, for example, any material that is to be used in the field of fluorescence detection and through which light passes should have sufficiently low fluorescence in the detected bandwidths so that background fluorescence does not interfere with detection of the signal from the sample material.

Curable bonding materials finding use in the invention include polymerizable adhesives and activatable adhesives.

Polymerizable adhesives are those adhesives made up of polymerizable components including monomeric, oligomeric and low molecular weight polymeric compounds, where oligomeric and low molecular weight polymeric compounds present in the adhesive materials will generally have a molecular weight that does not exceed about $10^6$, and usually does not exceed about $10^5$, and more usually does not exceed about $10^3$. The material may comprise one or a plurality of different types of polymerizable components, where when a plurality of different types of polymerizable components is present in the adhesive, the number of different components will generally not exceed 5 and will usually not exceed 3. The polymerizable components present in the polymerizable adhesives may be polymerizable by exposure to one or more of radiation (e.g., electron beam, W radiation, microwave radiation, $\gamma$-radiation), and/or heat, as will be described in greater detail below. A variety of polymerizable components may find use in the subject materials, based on any mode of polymerization mechanism (including condensation, free radical, ionic, ring opening) where the components may be acrylic, methacrylic, cyanoacrylic, epoxide base, two-component epoxy adhesives, two-component urethane adhesives, and the like. Specific polymerizable components of interest include methylmethacrylate, ethylene glycol methacrylate, tetraethylene glycol methacrylate, cyano acrylate, uretheane prepolymers and diols, epoxy-containing prepolymers with amines, and the like. In the subject polymerizable adhesives, the polymerizable compounds will generally make up at least about 1%, usually at least about 5%, and more usually at least about 10% by weight of the bonding material.

The polymerizable adhesive may include, in addition to the polymerizable components, one or more additional agents. One agent which may find use, depending on the particular adhesive employed, is a polymerization agent, where such agents include photosensitizers, photoinitiators, thermal initiators, and the like. Typical photosensitizers include the thioxantone derivatives; typical photoinitiators include benzophenone derivatives; and typical thermal initiators include the family of peroxy, perester, and azo initiators. When present, such polymerization agents will generally not make up more than about 5%, usually about 1% and more usually about 0.5% by weight of the bonding material.

Certain suitable polymerizable adhesive materials are commercially available, including for example (from Summers Corp., Fort Washington, Pa.): J91 (a single-component UV curable adhesive having a viscosity (uncured) of 250–300 cP; P92 (a single-component UV curable photopolymer having a viscosity (uncured) of 900–1400 cP; SK-9 (a single-component modified acrylate/methacrylate photopolymer having a viscosity (uncured) of 80–100 cP; DC-90 (a hybrid two-component UV sensitive cement having a viscosity (uncured) of 275–320 cP; EK-93 (a thixotropic two-component epoxy system having a viscosity of 25,000 cP; and (from Loctite Corp., Rocky Hill, Conn.): Depend 330 (a two-part mix acrylic thermocurable adhesive having a viscosity (uncured) greater than 10,000 cP.

Activatable adhesives finding use in the methods of the invention are those adhesives which include activatable polymeric compounds in combination with a carrier liquid. Depending on the particular adhesive, the polymeric compound may be dissolved in the carrier liquid (i.e., the carrier liquid is a solvent for the polymeric compound) or dispersed in the carrier liquid, such that the adhesive material is an emulsion or suspension of the polymeric compound in the carrier liquid. The number of different activatable polymeric compounds in the activatable adhesives may range from 0 to 3, and usually range from 0 to 2, more usually from 0 to 1. The activatable polymeric compounds will typically make up at least about 0%, usually at least about 5% and more usually at least about 10% by weight of the adhesive.

An activatable polymeric compound is a polymeric compound that is capable of being treated so as to serve as an agent capable of bonding or sealing two substrates together. Activatable polymeric compounds include compounds comprising activatable functional groups, where illustrative activatable functional groups include groups that can form strong interactive forces with the surface of the base substrate. Specific applicable groups can be hydrogen bonding forming groups such as the urethane containing polymers or halogen containing polymers, such as polyvinyl chloride. The activatable polymeric component includes small molecular weight polymers that upon application of heat or pressure diffuse or penetrate into the surface of the base material, creating sufficient physical adhesion to maintain the integrity of the microchannel structures. Activatable polymeric compounds include rubbery elastomeric materials such as, for example, silicone gums and resins, the styrene-butadiene copolymers, polychloroprene, neoprene, and the nitrile and butyl containing elastomeric polymers; polylacrylics; polyurethanes; polyamides; phenoxies; polyvinylacetals, and the like. Specific activatable polymeric compounds of interest include, for example: silicone gums, whereby upon application silicone polymers diffuse into the substrate surface, which can be thermocured after application to form crosslinked siloxane structures; urethane containing elastomers, which provide strong hydrogen bonding interaction with any polymer containing carboxyl groups, such as the acrylates; and nitrile containing polymers, which provide strong quasi-crosslinked intermolecular structures by dipole-dipole interaction of the nitrile groups.

The carrier liquid component of the activatable adhesive material may be any of a variety of different liquids, where the liquid is a liquid that is readily separable from the polymeric compound following application of the adhesive to the surface of the substrate. Illustrative liquids include solvents inert to the cover material that may be removed by evaporation, which may be carried out under low pressure. Carrier liquids will make up at least 50%, usually at least 25% and more usually at least 5%, by weight of the adhesive material.

Other components which may be present in the activatable adhesive include reaction catalysts, thermal initiators, and photoinitiators; where such components are present, they will usually be present in an amount which does not exceed 5%, more usually in an amount which does not exceed 1%, by weight of the adhesive material.

Following application of the layer of fluid curable adhesive to the surface of the substrate, the applied layer will be rendered non-flowable. By non-flowable is meant that the applied layer is thickened so that the viscosity of adhesive layer will be increased to at least about $10^5$ cP, in some embodiments at least about $10^6$ cP and in still other embodiments at least about $10^7$ cP. The manner by which the adhesive layer is rendered non-flowable will depend on the nature of the adhesive employed.

Thus, for polymerizable adhesives, the adhesive will be partially polymerized so that a sufficient percentage of the polymerizable components of the adhesive are polymerized to render the material suitably non-flowable and tacky. Generally, during partial polymerization at least about 50%, usually at least about 75% and not more than about 95%, usually not more than about 90% of the polymerizable components will be polymerized. Partial polymerization can be achieved using any convenient means, including radiation, heat, light, and the like.

For the activatable adhesives, the applied layer will be rendered suitably non-flowable by separating or removing the carrier liquid from the layer. Removal of carrier liquid may be accomplished using any convenient means, including evaporation, which may be carried out under low pressure, and the like.

After the applied layer has been rendered non-flowable, the surface of the first substrate (e.g., the cover) comprising the adhesive layer will then be contacted with the surface of the second substrate (e.g., the base plate) in which the microchannel or microchannels are formed. To assist in ensuring sufficient contact, pressure may be employed, as convenient.

Following contact, the thickened adhesive will be cured, resulting in the bonding of the first and second substrates and the production of a sealed microchannel structure. The manner by which curing of the thickened adhesive is accomplished will depend on the type of adhesive employed. Thus, for polymerizable adhesives, the adhesive layer will already be partially polymerized and final curing may be accomplished by one ore more of exposure to radiation, heat, light and the like. Alternatively, for the activatable polymeric adhesives, the adhesive layer positioned between the first and second substrates will then be treated to activate the adhesive, where treatment could include exposure of the layer to radiation, heat, and the like, depending on the particular nature of the adhesive.

Where desired the above method may be further modified to include a substrate pretreatment step prior to the application of the adhesive to the substrate. Pretreatment steps that find use include exposure of the substrate, either the first or second substrate, to a cleaning and/or abrasion agent, etching agent, e.g plasma, corona, chemical, and the like, where such pretreatments provide for improved wettability of the surface of the substrate by the adhesive material.

EXAMPLES

The following examples are offered by way of illustration and not by way of limitation.

Example 1

This Example illustrates fabrication of a microchannel structure made up of a polymethylmethacrylate base plate bonded to a polymethylmethacrylate cover using a photocurable acrylate bonding material in a two-step curing process.

In this example, the bonding material is prepared as a blend of linear low molecular weight polymethylmethacrylate (MW=$10^5$–$10^6$, 5–30% w/w) dissolved in a mixture of methylmethacrylate monomer (60–95% w/w), allylmethacrylate (1–5% w/w), and 0.5% w/w 2-hydroxy-2,2-dimethylactophenone (Darocure-1173, EM Industries) as a polymerization photoinitiator. Using spin coating tools, a thin layer (1–10 µm) of this bonding material is applied to the flat cover plate made of polymethylmethacrylate (PMMA). The coated cover is exposed for 10–30 seconds to a 15 watt fluorescent lamp at 1 inch from the surface. With this pre-curing step, the thin film has a non-flowable consistency, tacky toward the surface of a PMMA base plate with microchannel structures. The base plate is aligned and firmly positioned over the cover plate to form a base-to-cover sandwich, and 50–150 psi of pressure is applied to maintain the contact of base-to-cover and complete the bonding process by curing the acrylic interface under a 15 watt fluorescent lamp at 1 inch from the surface for 1–2 hours. The final cured interface provides a crosslinked, optically transparent cement between the cover and base plates, with good wall contact to the cover plate and open channels for analytical applications.

Example 2

This Example illustrates fabrication of a microchannel structure made up of a polymethylmethacrylate base plate bonded to a Mylar™ film cover using a thermally activated bonding material.

In this Example, the bonding material is a commercially-available thermally-activated adhesive. Photolithographic and electroforming techniques were used to prepare a mold, and injection molding techniques were used to prepare a microchannel base plate of an acrylic polymer (AtoHaas, Plexiglas™ V825NA-100). The microchannel structure in this Example corresponds to two crossed linear channels of dimensions 2 cm and 5.5 cm in length respectively. The channels have a trapezoidal cross-section, with widths measuring about 120 µm and about 30 µm, and with an average depth about 40 µm. At the termini of the channels, holes 3 mm in diameter were drilled through the base plate to serve as buffer reservoirs. The channels were covered by thermal lamination of a 2 mil thick sheet of Mylar™ coated with a thermally-activated adhesive (MonoKote™, made by Top Flight Co.) at 105° C. for 5 minutes. Electrodes of 76 micron diameter platinum wire were routed to each of the four reservoirs and terminated at one edge of the chip with a 4-prong 2.54 mm pitch KK® electrical heater (Waldon Electronics). No pretreatment or coating procedure was applied to the walls of the microchannel. The microchannel constructed this way has three walls whose surfaces are of acrylic polymer, formed from the base plate, and a fourth wall whose surface is formed of the MonoKote adhesive.

Example 3

This Example illustrates separation of the fragments in the HAE III digest of ΦX174 RF DNA by capillary electrophoresis in a sealed plastic PMMA/Mylar™ microchannel structure fabricated as described in Example 2.

Figure 7:
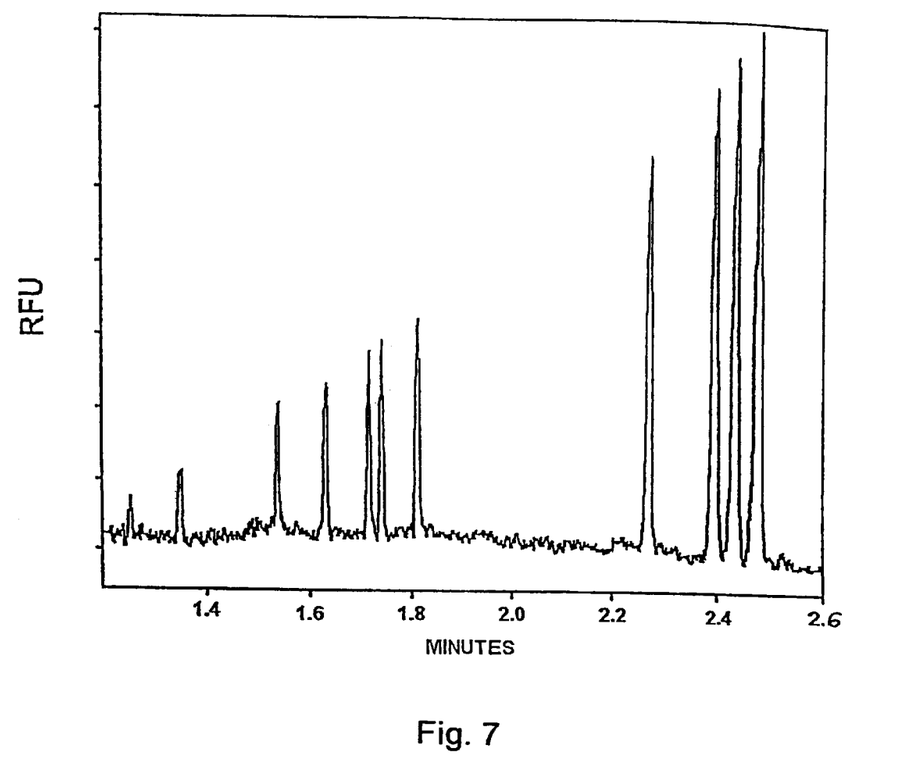
FIG. 7 shows results of electrophoretic separation of fragments in the HAE III digest of ΦX174 RF DNA in a sealed plastic PMMA/Mylar™ microchannel structure.

DNA separations were done in a sieving matrix consisting of 0.5% (w/v) hydroxyethylcellulose (HEC, MW 90,0000–105,0000), dissolved in 0.5X TBE with 2.5 µg/mL ethidium bromide. A sample of Hae III digest of ΦX174 RF DNA with fragments ranging in size 72 to 1354 base pairs previously diluted in run buffer was injected in the separation microchannel. After sample injection, separation of double stranded fragments was performed at an effective field strength of 190 V/cm. Fragment detection was performed through the PMMA base plate, using a fluorescence microscope (Olympus America) with photometer detection system (Photon Technology International). Excitation was derived from a deuterium lamp and delivered to the separation channel through a dichroic cube with 530 nm excitation filter, a 560–580 nm dichroic mirror, and a 590 nm long pass emission filter. Representative results of this separation are shown in FIG. 7 for an effective separation length of 4 cm with a total separation time of 2.6 minutes.

Example 4

This Example illustrates fabrication of a microchannel structure made up of a polymethylmethacrylate base plate covered with a film composite of a polyethylene (PE) and a polydimethylsiloxane (PDMS) elastomeric material in a two-step curing process.

In this Example, the cover film was prepared by applying a thin coat (about 100 $\mu$m) of Sylgard 184 (PDMS, Dow Corning) to a 2 mil thick polyethylene film (Barrier Films). The elastomeric layer of PDMS was pre-cured for 30 minutes in air at room temperature. The resulting pre-cured PE/PDMS composite was applied to a polymethylmethacrylate microchannel base plate made by injection molding as described in Example 2, and the PDMS allowed to cure further for 24 hours at room temperature. No pretreatment or coating procedure was applied to the walls of the microchannel. The microchannel constructed this way has three walls whose surfaces are of acrylic polymer, formed from the base plate, and a fourth wall whose surface is formed of the PDMS elastomeric material.

Example 5

This Example illustrates separation of the fragments in the HAE III digest of ΦX174 RF DNA by capillary electrophoresis in a sealed plastic PMMA/PDMS microchannel structure fabricated as described in Example 4.

Figure 8:
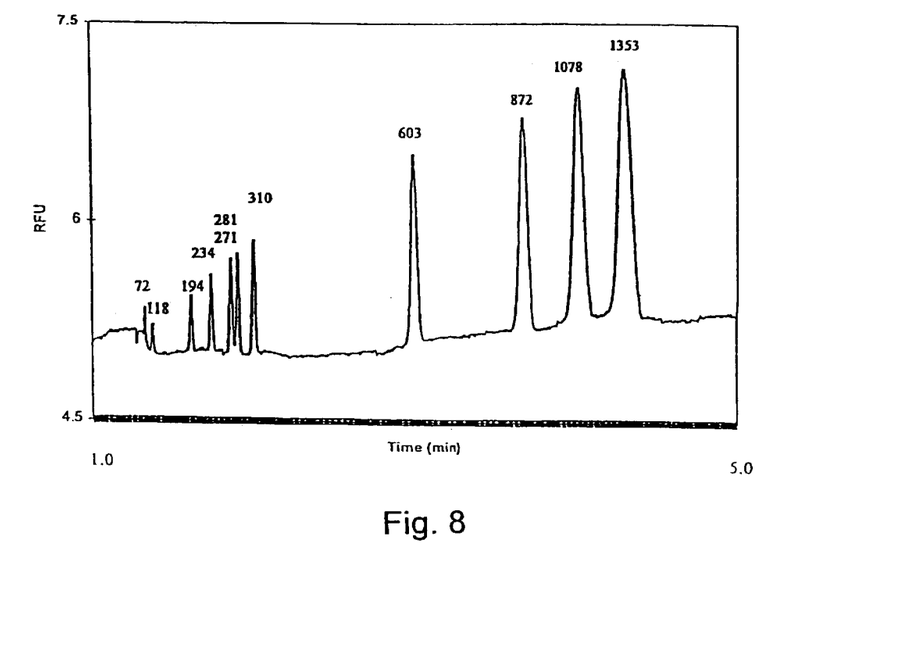
FIG. 8 shows results of electrophoretic separation of fragments in the HAE III digest of ΦX174 RF DNA in a sealed plastic PMMA/PDMS microchannel structure.
Figure 9:
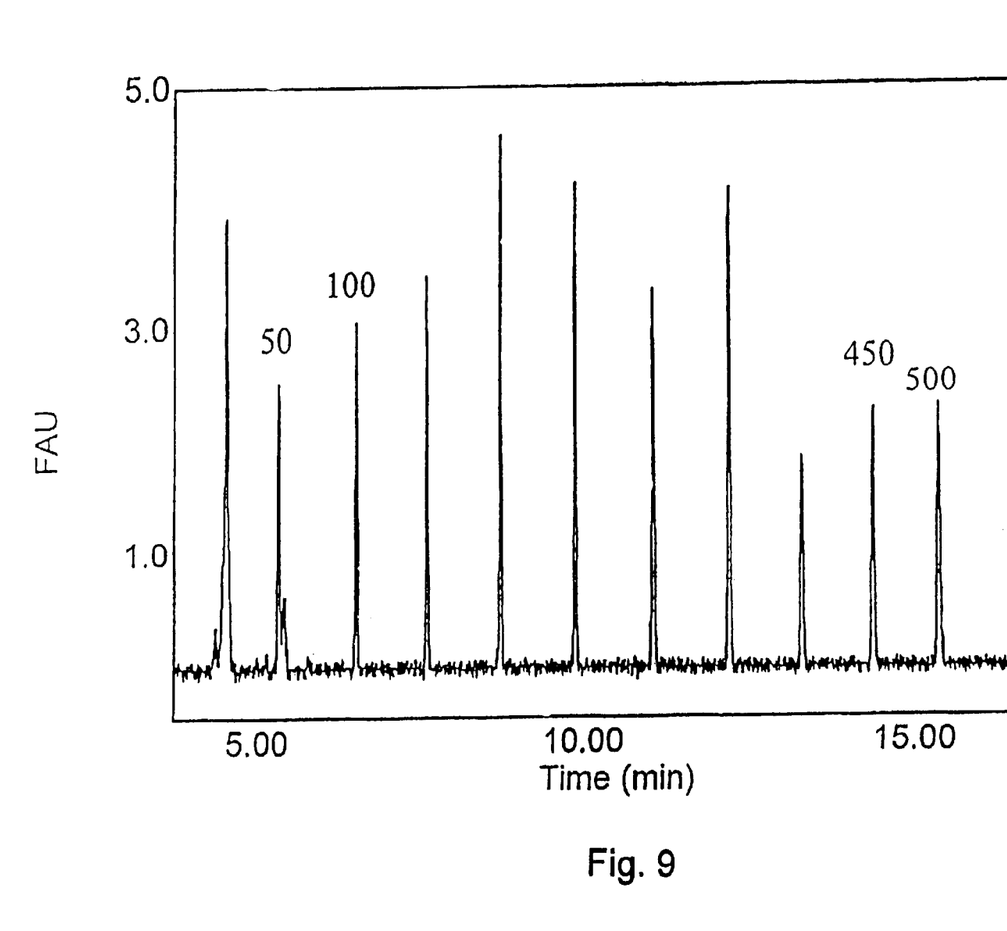
FIG. 9 provides results of electrophoretic separation of single stranded DNA fragments having sizes from 50 to 500 bases at 50-base intervals in a thermobonded PMMA/PMMA microchannel structure.

In this Example, the experimental parameters and conditions for the electrophoresis separation and detection of the Hae III digest of ΦX174 RF DNA fragments under non-denaturing conditions were as in Example 3. Results of the separation using the PMMA/PDMS microchannel structures are shown in FIG. 8. In this Example, separation of the eleven double stranded fragments was achieved in 5.0 minutes of total separation time.

Example 6

This Example illustrates fabrication of a microchannel structure made up of a polymethylmethacrylate base plate bonded to a polymethylmethacrylate cover using a thermally curable bonding material in a one-step curing process.

In this example, the bonding material is prepared as a mixture of linear low molecular weight polymethylmethacrylate (MW=$10^5$–$10^6$, 5–30% w/w) in methylmethacrylate monomer (70–95% w/w), and t-butylperoxypivalate (tBPP, Lupersol 11-Pennwalt) as a thermal polymerization initiator. Using spin coating tools, a thin layer (1–10 $\mu$m) of this bonding material is applied to a flat cover plate made of polymethylmethacrylate (PMMA). The base plate is aligned and firmly positioned over the cover plate to form a base-to-cover sandwich in a fixture, and pressure is applied using the fixture (50–150 psi) to maintain the contact of base-to-cover. The assembly of base-to-cover is carried out in a manner that avoids overflow of the channels with the bonding material. The bonding process is completed by curing the acrylic interface at 70° C. for 1–2 hours.

Example 7

This Example illustrates fabrication of a microchannel structure made up of a polymethylmethacrylate base plate bonded to a polymer film cover using a thermally curable bonding material in a one-step curing process.

In this Example a process similar to that of Example 6 is employed, by substitution of a cover film of 50–500 $\mu$m thickness for the PMMA cover plate. Films made of hydrocarbon based polymers (e.g., low density polyethylene, amorphous polypropylene), fluorinated polymers (e.g., polytetrafluoroethylene), or copolymers or blends of such polymers are suitable for this process and provide added optical transparency required for spectroscopic (fluorescence and UV) detection through the cover. Chemical bonding of the acrylic base to the cover film is carried out generally as described above for the acrylic flat cover. In this format, the application of the bonding material to the cover film can be carried out manually, for example using a fine paint brush or rollers, or automatically, for example using roll coaters or float coaters.

Example 8

This Example illustrates fabrication of a microchannel structure made up of a polymethylmethacrylate base plate bonded to a polymethylmethacrylate cover using a thermally curable bonding material using a one-step curing process.

A chemical bonding material was prepared as a mixture of linear low molecular weight polymethylmethacrylate (Mw=$10^5$–$10^6$, 15% w/w) in methylmethacrylate monomer (85% w/w), and t-butylperoxypivalate (tBPP, Lupersol 11, Penwalt) as a thermal polymerization initiator.

The microchannel structure was prepared from a base plate in which microchannels were formed, with recess wells bored partway through the base plate at the ends of the channels. The cover plate is provided with 2 mm diameter holes that align with the recess wells at the ends of the channels when the cover plate and base plate are apposed. The base plate and cover plate were made by injection molding from a polymethylmethacrylate resin (AtoHaas V825-NA100). After careful cleaning of the bonding surfaces with a surfactant containing solution, the curable bonding solution prepared as described above was applied onto the cover plate using standard spin coating equipment at 2000 rpm for 5 sec. The base plate was then carefully aligned onto the coated cover, with the apposing generally planar surfaces face-to-face. The sandwich structure assembled this way was then placed in a bonding fixture, configured to apply uniform pressure throughout the assembled structure. The interface layer is allowed to cure between the two plates under pressure of 40 psi in the fixture at 70° C. in an oven for two hours. After this curing process, the fixture containing the structure is cooled, and then the bonded microchannel structure is removed from the fixture in its final functional form.

The channel pattern used in this Example has a crossed-channel configuration, with reservoir wells at the ends of the channels. The shorter channel has a segment of length 0.4 cm from the well to the intersection on one side, and a segment of length 1.0 cm from the well to the intersection on the other side. The longer channel has segments of lengths 1 cm and 5 cm respectively from the well to the intersection. The channel cross-section has an asymmetrical trapezoidal shape of about 40 μm at the bottom of the channel and about 100 μm at the top of the channel. The channel depth after bonding was 35 μm as measured in scanning electron micrographs.

Example 9

This Example illustrates separation of a DNA ladder under denaturant conditions by capillary electrophoresis in a sealed plastic PMMA/PMMA microchannel structure constructed as described in Example 8.

Without any preconditioning of the microchannel surface, the microchannels were filled with a 5% linear polyacrylamide (MW=2–3×10$^6$) solution in 1×TBE buffer and 7 M urea using a pressurized syringe loading device with liquid tight connections to the well at the end of the long arm of the long channel. A solution of GeneScan 500 DNA ladder with tagged TAMRA label was electrokinetically injected into the channel cross-section from the short arm of the short channel. After a sample plug was formed at the channel intersection, a separation voltage of 200 V/cm was applied between the two wells of the long channel using platinum wire electrodes (76 μm). Detection of the separating bands in the longer segment of the longer channel was performed using a fluorescence microscope (Olympus America) with photometer detection system (Photon Technology International). Excitation was derived from mercury lamp and delivered to the separation channel through a dichroic cube with 535–550 nm excitation filter, a 560–580 nm dichroic mirror, and a 570 nm long pass emission filter.

Figure 10:
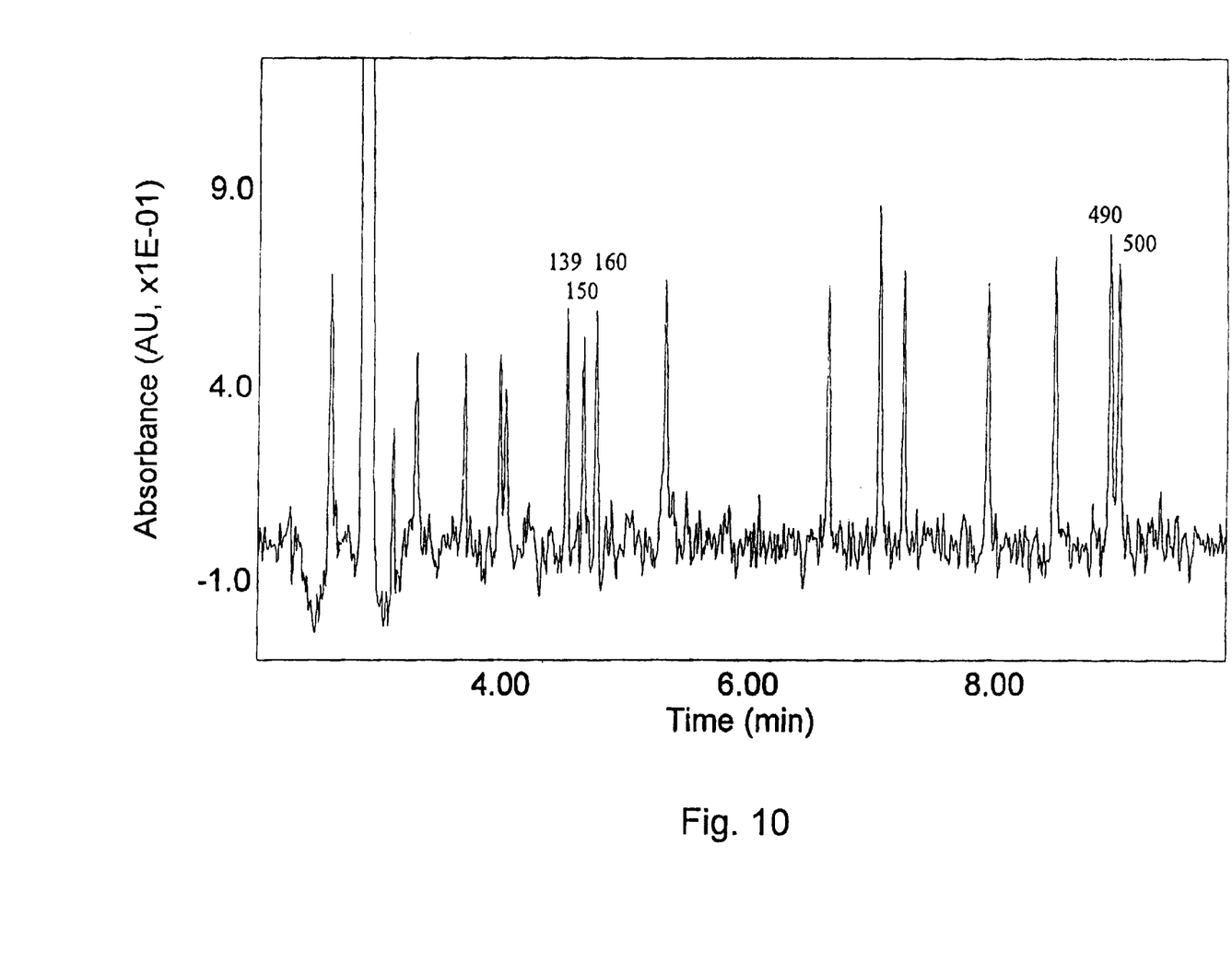
FIG. 10 provides results of electrophoretic separation of single stranded DNA fragments having sizes from 35 to 500 bases in a PMMA/PMMA microchannel structure bonded using a thermally activated polymerizable bonding material.

Representative results of separations made in this way are shown in FIG. 10. The effective length of the separation is 4 cm, and separation was achieved in a total separation time of 7.5 minutes. The GeneScan 500 ladder sample contains 16 DNA fragments with different number of incremental bases from each fragment. Fragment separation of fragments differing by 10 bases are labeled in the electropherogram of FIG. 10. Normalized single base resolution was calculated at between 0.3 and 1.2 for the 35 to 500 bases separation range.

It is evident from the above results and discussion that improved methods for fabricating polymeric microchannel structures suitable for use in electrofluidic applications are provided. By using the subject methods, cover and base plate components of the structures can be sealed together without deformation, partial or complete clogging of the enclosed microchannels.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for constructing an enclosed microchannel structure comprising the steps of providing a substantially planar base substrate fabricated of a plastic material and having at least one substantially planar surface, forming in said base substrate at least one microchannel of capillary dimensions which opens onto said surface, providing a substantially planar cover substrate having at least one substantially planar surface, applying a bonding material to at least one of the surfaces, partially curing the bonding material and apposing said surface of said cover substrate and said surface of said base substrate whereby a stable interface applying a bonding material to at least one of the surfaces, partially curing the bonding material and between said apposed surfaces with the cured bonding material.

2. The method of claim 1 wherein said surface of said cover substrate is fabricated of a plastic material and wherein said apposing step includes the step of pressing said apposed surfaces together and heating said substrates for a time and to a temperature sufficient to bond said surfaces together.

3. The method of claim 1 wherein the applying step includes the step of applying the bonding material to said surface of said cover substrate.

4. The method of claim 1 wherein said cured bonding material comprises an elastomeric adhesive material.

5. The method of claim 1 wherein said bonding material comprises a thermo-melting bonding material and wherein said apposing step includes the step of heating said bonding material to a temperature and for a time sufficient to melt said bonding material and then cooling said bonding material between said apposed surfaces to permit the bonding material to harden.

6. The method of claim 1 wherein said bonding material comprises an activatable bonding material.

7. The method of claim 1 wherein said bonding material comprises a curable bonding material.

8. The method of claim 1 wherein said bonding material comprises a polymerizable bonding material.

9. The method of claim 7 wherein said applying step includes the step of applying the bonding material to said surface in a flowable state and wherein said partially curing step includes the step of partially curing the bonding material to a non-flowable state.

10. The method of claim 8 wherein said bonding material further comprises a polymerization initiator.

11. The method of claim 10 wherein said polymerization initiator comprises a photoinitiator and wherein said apposing step includes the step of exposing said bonding material between said apposed surfaces to light at a wavelength and intensity and for a time sufficient to cause polymerization.

12. The method of claim 10 wherein said polymerization initiator comprises a thermal initiator and wherein said apposing step includes the step of heating said bonding material between said apposed surfaces to a temperature and for a time sufficient to cause polymerization.

13. The method of claim 1 wherein said cover substrate comprises an elastomeric material.

14. A method for constructing an enclosed microchannel structure comprising the steps of providing a substantially planar base substrate fabricated of a plastic material and having at least one substantially planar surface, forming in said base substrate first and second microchannels of capillary dimensions which meet at an intersection and each open onto said surface, providing a substantially planar cover substrate having at least one substantially planar surface, applying a bonding material to at least one of the sufaces, partially curing the bonding material and apposing said surface of said cover substrate and said surface of said base substrate and causing formation of a stable interface between said apposed surfaces.

15. The method of claim 14 wherein the first and second microchannels are each provided with first and second end portions, further comprising the step of forming first and second wells in at least one of the base substrate and the cover substrate for each of the first and second microchannels, the first and second wells of each microchannel communicating with the respective first and second end portions of said microchannel.

16. The method of claim 15 further comprising the step of electrically coupling an electrode to each of the first and second wells.

17. The method of claim 14 further comprising the steps of applying a bonding material to at least one of the surfaces and partially curing the bonding material prior to the apposing step.

* * * * *